(12) United States Patent
Amrich et al.

(10) Patent No.: US 6,599,322 B1
(45) Date of Patent: Jul. 29, 2003

(54) METHOD FOR PRODUCING UNDERCUT MICRO RECESSES IN A SURFACE, A SURGICAL IMPLANT MADE THEREBY, AND METHOD FOR FIXING AN IMPLANT TO BONE

(75) Inventors: Mark P. Amrich, Tyngsborough, MA (US); Joseph Buturlia, West Boxford, MA (US); Robert F. Lynch, Newburyport, MA (US); Jonathan L. Rolfe, North Easton, MA (US)

(73) Assignee: Tecomet, Inc., Wilmington, MA (US)

( * ) Notice: Subject to any disclaimer, the term of this patent is extended or adjusted under 35 U.S.C. 154(b) by 0 days.

(21) Appl. No.: 09/976,722

(22) Filed: Oct. 12, 2001

Related U.S. Application Data

(60) Provisional application No. 60/264,084, filed on Jan. 25, 2001, and provisional application No. 60/309,923, filed on Aug. 3, 2001.

(51) Int. Cl.⁷ .................................................. A61F 2/28
(52) U.S. Cl. ................ 623/23.5; 623/23.74; 623/23.29; 623/20.17
(58) Field of Search ................................ 623/1.39, 1.4, 623/20.17, 23.24, 23.29, 23.3, 23.31, 23.5, 23.55, 23.74, 23.76

(56) References Cited

U.S. PATENT DOCUMENTS

| | | |
|---|---|---|
| 852,873 A | 5/1907 | Davidson |
| 3,045,321 A | 7/1962 | McDermott ................. 29/78 |
| 3,359,192 A | 12/1967 | Heinrich et al. ............ 204/143 |
| 3,605,123 A | 9/1971 | Hahn |
| 3,679,500 A | 7/1972 | Kubo et al. |
| 3,905,080 A | 9/1975 | Bond |
| 4,033,831 A | 7/1977 | Bakewell |
| 4,069,085 A | 1/1978 | Buysman et al. |
| 4,272,855 A | 6/1981 | Frey ............................ 3/1.9 |
| 4,284,468 A | 8/1981 | Stearns |
| 4,330,891 A | 5/1982 | Branemark et al. |
| 4,355,428 A | 10/1982 | Deloison et al. |
| 4,422,465 A | 12/1983 | Haga |
| 4,456,500 A | 6/1984 | Ibata |
| 4,470,872 A | 9/1984 | Sudo et al. ................. 156/630 |
| 4,528,070 A | 7/1985 | Gamblin |
| 4,608,052 A | 8/1986 | Van Kampen et al. ........ 623/22 |
| 4,632,726 A | 12/1986 | Thoms |
| 4,634,603 A | 1/1987 | Gruss et al. |
| 4,644,942 A | 2/1987 | Sump ........................... 623/16 |
| 4,662,984 A | 5/1987 | Ohtake et al. |
| 4,664,668 A | 5/1987 | Beck et al. |
| 4,673,409 A | 6/1987 | Van Kampen |
| 4,714,470 A * | 12/1987 | Webb, Jr. et al. ............ 623/18 |
| 4,725,334 A | 2/1988 | Brimm |
| 4,752,294 A | 6/1988 | Lundgren |
| 4,803,098 A | 2/1989 | Henri et al. |
| 4,834,756 A | 5/1989 | Kenna ......................... 623/16 |

(List continued on next page.)

FOREIGN PATENT DOCUMENTS

| | | |
|---|---|---|
| GB | 2 206 614 A | 1/1989 |
| JP | 06125978 | 5/1994 |

OTHER PUBLICATIONS

International Search Report, International Ser. No. PCT/US02/02066, Filing date Jan. 25, 2002.

International Search Report, International Ser. No. PCT/US02/13618, Filing date Apr. 30, 2002.

*Primary Examiner*—Corrine McDermott
*Assistant Examiner*—Cheryl Miller
(74) *Attorney, Agent, or Firm*—Morgan, Lewis & Bockius, LLP

(57) ABSTRACT

A surgical implant having a datum surface for engaging tissue. Embodiments of the surgical implant include a recess in an original datum surface having a sharp undercut ovoid configuration and a multiplicity of recesses that are interconnected.

6 Claims, 5 Drawing Sheets

U.S. PATENT DOCUMENTS

| | | | |
|---|---|---|---|
| 4,836,837 A | 6/1989 | Rapp | |
| 4,836,884 A | 6/1989 | McAuslan | |
| 4,846,839 A * | 7/1989 | Noiles | 623/18 |
| 4,851,008 A | 7/1989 | Johnson | |
| 4,863,474 A | 9/1989 | Brown et al. | |
| 4,863,475 A | 9/1989 | Andersen et al. | |
| 4,865,603 A | 9/1989 | Noiles | |
| 4,871,366 A | 10/1989 | von Recum et al. | |
| 4,900,387 A | 2/1990 | Johnson | |
| 4,900,398 A | 2/1990 | Chen | |
| H788 H | 6/1990 | Schneider | 156/634 |
| 4,944,763 A | 7/1990 | Willert et al. | |
| 4,955,909 A | 9/1990 | Ersek et al. | |
| 4,959,275 A | 9/1990 | Iguchi et al. | |
| 4,960,381 A | 10/1990 | Niznick | |
| 4,969,904 A | 11/1990 | Koch et al. | |
| 4,976,738 A | 12/1990 | Frey et al. | |
| 4,978,358 A | 12/1990 | Bobyn | |
| 4,989,304 A | 2/1991 | Sonefors | |
| 5,002,572 A | 3/1991 | Picha | |
| 5,002,575 A | 3/1991 | Johnson | 623/16 |
| 5,002,580 A | 3/1991 | Noble et al. | |
| 5,007,931 A | 4/1991 | Smith | |
| 5,011,494 A | 4/1991 | von Recum et al. | |
| 5,100,508 A | 3/1992 | Yoshida et al. | |
| 5,108,434 A | 4/1992 | Ahrens et al. | |
| 5,139,528 A | 8/1992 | Koch et al. | |
| 5,207,709 A | 5/1993 | Picha | |
| 5,219,361 A | 6/1993 | von Recum et al. | |
| 5,222,983 A | 6/1993 | Schmitz et al. | |
| 5,236,459 A | 8/1993 | Koch et al. | |
| 5,246,530 A | 9/1993 | Bugle et al. | 156/643 |
| 5,258,098 A | 11/1993 | Wagner et al. | 156/645 |
| 5,268,068 A | 12/1993 | Cowell et al. | |
| 5,271,736 A | 12/1993 | Picha | |
| 5,298,115 A | 3/1994 | Leonard | 156/645 |
| 5,307,594 A | 5/1994 | Panchison | |
| 5,358,533 A | 10/1994 | Noiles et al. | |
| 5,456,723 A | 10/1995 | Steinemann et al. | 623/16 |
| 5,484,074 A | 1/1996 | Deibler et al. | |
| 5,507,815 A | 4/1996 | Wagner et al. | 623/16 |
| 5,526,950 A | 6/1996 | Tago et al. | |
| 5,549,704 A | 8/1996 | Sutter | 623/23 |
| 5,571,017 A | 11/1996 | Niznick | |
| 5,603,338 A | 2/1997 | Beaty | 128/898 |
| 5,606,589 A | 2/1997 | Pellegrino et al. | 378/154 |
| 5,607,480 A | 3/1997 | Beaty | |
| 5,639,237 A | 6/1997 | Fontenot | |
| 5,645,593 A | 7/1997 | Woods et al. | |
| 5,658,334 A | 8/1997 | Caldarise et al. | 623/16 |
| 5,665,118 A | 9/1997 | LaSalle et al. | 623/16 |
| 5,665,121 A | 9/1997 | Gie et al. | |
| 5,676,850 A | 10/1997 | Reed et al. | |
| 5,709,804 A | 1/1998 | Makita et al. | |
| 5,713,410 A | 2/1998 | LaSalle et al. | 164/516 |
| 5,716,412 A | 2/1998 | DeCarlo, Jr. et al. | 623/16 |
| 5,728,159 A | 3/1998 | Stroever et al. | |
| 5,730,887 A | 3/1998 | Simpson et al. | |
| 5,814,235 A | 9/1998 | Pellegrino et al. | 216/12 |
| 5,826,586 A | 10/1998 | Mishra et al. | |
| 5,830,373 A | 11/1998 | Ohtake et al. | |
| 5,843,250 A | 12/1998 | Bone et al. | |
| 5,853,561 A | 12/1998 | Banks | 205/646 |
| 5,897,592 A | 4/1999 | Caldarise et al. | |
| 5,910,173 A | 6/1999 | DeCarlo, Jr. et al. | 623/66 |
| 5,922,029 A | 7/1999 | Wagner et al. | 623/66 |
| 5,965,006 A | 10/1999 | Baege et al. | 205/666 |
| 5,975,903 A | 11/1999 | Shoher et al. | |
| 6,005,164 A | 12/1999 | Johansson et al. | 623/16 |
| 6,008,430 A | 12/1999 | White | |
| 6,008,431 A | 12/1999 | Caldarise et al. | 623/16 |
| 6,008,432 A | 12/1999 | Taylor | |
| 6,010,336 A | 1/2000 | Shimotoso et al. | |
| 6,069,295 A | 5/2000 | Leitao | |
| 6,095,817 A | 8/2000 | Wagner et al. | |
| 6,106,558 A | 8/2000 | Picha | |
| 6,149,688 A | 11/2000 | Brosnahan et al. | |
| 6,149,689 A | 11/2000 | Grundei | |
| 6,171,344 B1 | 1/2001 | Atala | |
| 6,193,762 B1 | 2/2001 | Wagner et al. | 623/66 |
| 6,200,346 B1 | 3/2001 | Baege et al. | 623/11.11 |
| 6,217,333 B1 | 4/2001 | Ercoli | |
| 6,217,615 B1 | 4/2001 | Sioshansi et al. | |
| 6,221,109 B1 | 4/2001 | Geistlich et al. | |
| 6,235,638 B1 | 5/2001 | Huang et al. | 438/695 |
| 6,261,322 B1 | 7/2001 | Despres, III et al. | |
| 6,270,530 B1 | 8/2001 | Eldridge et al. | |
| 6,277,150 B1 | 8/2001 | Crawley et al. | |
| 6,312,612 B1 | 11/2001 | Sherman et al. | |
| 6,315,798 B1 | 11/2001 | Ashby et al. | |
| 6,344,061 B1 | 2/2002 | Leitao et al. | |
| 2001/0039454 A1 | 11/2001 | Ricci et al. | |

* cited by examiner

PRESS FIT DIRECTION →

METHOD FOR PRODUCING UNDERCUT MICRO RECESSES IN A SURFACE, A SURGICAL IMPLANT MADE THEREBY, AND METHOD FOR FIXING AN IMPLANT TO BONE

CROSS-REFERENCE TO RELATED APPLICATIONS

This application claims the benefit of U.S. Provisional Patent Application Serial No. 60/264,084, filed Jan. 25, 2001, and U.S. Provisional Patent Application Serial No. 60/309,923, filed Aug. 3, 2001.

BACKGROUND OF THE INVENTION

1. Field of the Invention

The invention relates to the production of textured surfaces for medical and industrial applications and is directed more particularly to the production of undercut micro recesses in a surface, a surgical implant made thereby, and a method for fixing an implant to bone.

2. Description of the Prior Art

It is known to use textured surfaces on surgical implants for the purpose of encouraging bone adhesion and thus stabilize the location of the implant relative to the bone. For example, in an artificial hip, consisting of a femoral sub-assembly for positioning in a patient's femur, and an acetabular sub-assembly for positioning in the patient's acetabulum, the femoral sub-assembly includes an artificial stem which is typically provided with a textured surface, and the acetabular sub-assembly includes an acetabular cup which is typically provided with a textured surface, the textured surfaces being provided to promote bone in-growth.

The desirability of roughened, textured, bone-engaging surfaces to assure stable positioning of surgical implants has been recognized in U.S. Pat. No. 5,298,115, issued Mar. 29, 1994, in the name of Ian Leonard, U.S. Pat. No. 5,456,723, issued Oct. 10, 1995, in the name of Samuel G. Steinemann, U.S. Pat. No, 5,603,338, issued Feb. 18, 1997, in the name of Keith D. Beaty, U.S. Pat. No. 5,853,561, issued Dec. 29, 1998, in the name of Bruce A. Banks, and U.S. Pat. No. 5,965,006, issued Oct. 12, 1999, in the names of Roland Baege et al.

To produce such textured surfaces, one known method is to provide a mass of titanium spheres vacuum fused onto the datum surface of the implant. This method is described in U.S. Pat. No. 4,834,756, issued May 30, 1989, to Robert V. Kenna. In a similar procedure, described in U.S. Pat. No. 4,644,942, issued Feb. 24, 1987 to Kenneth R. Sump, an extractable component and titanium spheres are densified as a coating, which is fused onto a datum surface of the implant, and the extractable component subsequently is extracted. While an improvement over untreated metal, questions have arisen over the longevity of usefulness of the implanted devices utilizing such surfaces. It is questionable whether there is substantial genuine adhesion. It is believed that the voids formed by the spheres are not sufficient for long-term nourishment of ingrowing tissue and/or bone. Further, there have been failures of prosthetics treated in this manner because of the fusing process adversely affecting metallurgical properties of the implant material, and because of difficulties in removing manufacturing contaminants, such as cutting oils, from the fused sphere network. Still further, the original datum surface, which can be accurately determined, is lost by the application of the coating spheres.

The formation of perforated thin metallic sheets or plates by means of chemical milling and/or photo-chemical etching techniques has been described in U.S. Pat. No. 3,359,192, issued Dec. 19, 1967, in the names of Hans-Joachim Heinrich et al, U.S. Pat. No. 5,606,589, issued Feb. 25, 1997, in the names of Anthony J. Pellegrino et al, and U.S. Pat. No, 5,814,235, issued Sep. 29, 1998, in the names of Anthony J. Pellegrino et al. The processes therein described have been found lacking in precise control over the degree and extent of roughness or texturing.

In U.S. Pat. No. 5,258,098, issued Nov. 2, 1993, to Donald J. Wagner et al, U.S. Pat. No. 5,507,815, issued Apr. 16, 1996, to Donald J. Wagner et al, and U.S. Pat. No. 6,193,762, issued Feb. 27, 2001, in the names of Donald J. Wagner, et al, there are described chemical and electrochemical etching processes used in conjunction with random sprayed patterns of maskant to create a pattern of dots resistant to etching. After etching and maskant stripping repeatedly, a complex pattern is produced. While complex in appearance, such patterns offer little predictability and repeatability between implants, and lack engineered datum points.

Accordingly, there remains a need for a method for producing an engineered textured surface for interlocking with an adjacent body, such as a bone or other ingrowing body.

SUMMARY OF THE INVENTION

An object of the invention is, therefore, to provide a method for producing a textured surface which is adapted to interlock with an adjacent body.

A further object is to provide a method for producing undercut micro recesses in a surface of a body.

A still further object is to provide a method for producing such recesses in a desired pattern which is measurable and predictable, and which can be duplicated and repeated precisely in any selected number of surfaces.

A still further object is to provide a method for producing a surgical implant device wherein the material of the device retains its metallurgical properties throughout production.

A still further object is to provide a method for producing textured surfaces for surgical implants, which surfaces promote the ingrowth of tissue and/or bone to securely interconnect the implant and the tissue and/or bone.

A still further object is to provide a method for producing such surfaces which include undercut and interconnecting recesses which promote and facilitate ingrowth of bone and which, upon implantation, facilitate a "scratch fit" with bone, to stabilize the position of the surface on the bone and to initiate an interconnection process between the implant and the bone. The "scratch fit" is accomplished by the textured surface scraping bone from the implant site during a press fit implantation, thereby producing autografted bone in the voids of the textured surface.

A still further object of the invention is to provide methods for attaching a surgical implant to bone.

A still further object of the invention is to provide a method for bone harvesting and seeding of a surgical implant with particulate bone matter during attachment of the implant to the bone.

A still further object is to provide a method for making a surgical implant which exhibits a precise fit with a bone implant site, to reduce micro-motion between the implant and the bone site.

A still further object of the invention is to provide a surgical implant having undercut micro recesses with sharply defined edges in a bone-engaging surface thereof.

With the above and other objects in view, a feature of the invention is the provision of a method for producing a multiplicity of undercut micro recesses in a surface of an article, such that the article thereby exhibits a greater fractal area at a level below the surface than is exhibited at the surface, the method comprising the steps of applying a maskant layer to substantially an entirety of the article surface, removing the maskant layer in selected loci to expose underlying portions of the article surface in a selected, predictable, and reproducible pattern, applying an etchant to the exposed underlying surface portions for a time sufficient to etch the exposed surface portions and to enable the etchant to etch beneath remaining portions of the maskant layer and produce a multiplicity of undercut recesses, and removing the remaining maskant layer portions to provide the article surface in exposed condition with the multiplicity of recesses undercut and comprising interconnected recesses, to provide an engineered pattern of the recesses.

In accordance with a further feature of the invention, there is provided a method for producing a multiplicity of undercut micro recesses in a surface of an article in a selected pattern which can be repeated in any selected number of surfaces. The method includes the steps of applying a maskant layer to substantially an entirety of a selected surface of the article. The maskant layer is then removed by computer-directed laser ablation in programmed loci to expose underlying portions of the surface of the article in a programmed pattern. An etchant is then applied to the exposed underlying surface portions for a time sufficient to etch the exposed surface portions and to enable the etchant to etch beneath remaining portions of the maskant layer and produce the multiplicity of undercut recesses, and the remaining maskant layer is removed to provide the selected surface in exposed condition with the multiplicity of undercut recesses therein.

In accordance with a further feature of the invention, there is provided a method for producing a surgical implant having facility for stimulating ingrowth of bone upon attachment of the implant to a bone. The method includes the steps of providing a rigid article, applying a maskant layer to substantially an entirety of a datum surface of the article, removing portions of the maskant layer in selected loci to expose underlying portions of the surface of the article, applying an etchant to the exposed underlying surface portions for a time sufficient to etch the exposed surface portions and to enable the etchant to etch beneath remaining portions of the maskant layer and produce a multiplicity of undercut recesses having sharp edges at their intersections with the datum surface, and removing the remaining portions of the maskant layer to provide the datum surface in exposed condition with the sharp edges for shaving particulate matter from the bone, and with the recesses for receiving and retaining the bone particulate matter for stimulating ingrowth of bone.

In accordance with a still further feature of the invention, there is provided a method for producing a textured surface in a surgical implant. The method includes the steps of applying a maskant layer to substantially an entirety of a datum surface of the implant, removing portions of the maskant layer in selected loci to expose underlying portions of the datum surface of the implant, applying an etchant to the exposed underlying datum surface portions for a time sufficient to etch the exposed surface portions and to enable the etchant to etch beneath remaining portions of the maskant layer and produce a multiplicity of undercut recesses having sharp edges at their intersections with the datum surface, and removing the remaining portions of the maskant layer to provide the datum surface in exposed condition with the sharp edges for shaving particulate matter from the bone, and with the recesses for receiving and retaining the bone particulate matter for stimulating ingrowth of bone.

In accordance with a still further feature of the invention, there is provided a method for attaching a surgical implant to a bone, the method comprising the steps of providing a surgical implant having a datum surface, a multiplicity of micro recesses in the datum surface, and bone milling structure on the datum surface, pressing the datum surface against a surface of the bone, and urging the implant along the bone surface to mill particulate bone matter from the bone, wherein the recesses receive and retain the particulate bone matter to stimulate ingrowth of the bone.

In accordance with a still further feature of the invention, there is provided a method for attaching a surgical implant to a bone, the method comprising the steps of providing a surgical implant having a datum surface and a multiplicity of undercut microrecesses in the datum surface, such that the implant exhibits a greater fractal area at the level below the datum surface than is exhibited at the datum surface, intersections of the datum surface and the recesses defining sharp edges, pressing the datum surface against a surface of the bone, and urging the implant along the bone surface, to cause the sharp edges to shave particulate bone matter from the bone, wherein the recesses receive and retain the particulate bone matter to stimulate ingrowth of the bone.

In accordance with a still further feature of the invention, there is provided a method for bone harvesting and seeding of a surgical implant with particulate bone matter during attachment of the implant to the bone, the method comprising the steps of providing a surgical implant having a surface for engagement with a bone surface, the implant having a multiplicity of undercut micro recesses and bone milling structure in the surface thereof, and moving the implant along the bone, such that the milling structure dislocates particulate bone matter from the bone, the bone matter falling into the micro recesses and retained thereby to stimulate ingrowth of the bone into the undercut recesses.

In accordance with a still further feature of the invention, there is provided a method for making a surgical implant having generally opposed datum surfaces spaced from each other by a predetermined distance, each of the datum surfaces being adapted to interlock with a bone surface, the method comprises the steps of providing an article having first and second datum surface portions adapted to respectively engage first and second bone surfaces, the datum surface portions being spaced from each other by the predetermined distance which is substantially equal to a distance between the first and second bone surfaces, applying a maskant layer to substantially an entirety of each of the datum surfaces, removing the maskant layers in selected loci to expose underlying portions of the datum surfaces in a selected pattern, applying an etchant to the exposed underlying datum surface portions for a time sufficient to etch the exposed portions of the datum surfaces and to enable the etchant to etch beneath the remaining maskant layers and produce undercut recesses, and removing the remaining maskant to provide the opposed datum surfaces in exposed condition with the multiplicity of undercut recesses and devoid of structure protruding therefrom.

In accordance with a still further feature of the invention, there is provided a surgical implant comprising an article having a datum surface for abutting engagement with a bone, and a multiplicity of undercut micro recesses in the datum surface, such that the body exhibits a greater fractal area at a level below the surface than is exhibited at the surface. Intersections of the recesses and the datum surface define sharp edges adapted to cut the bone and produce bone particulates. The recesses are adapted to receive and retain the bone particulates cut from the bone by the edges, to stimulate ingrowth of the bone into the recesses.

The above and other features of the invention, including various novel details of components and method steps, will now be more particularly described with reference to the accompanying drawings and pointed out in the claims. It will be understood that the particular methods and devices embodying the invention are shown and described by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings.

DESCRIPTION OF THE PREFERRED EMBODIMENTS

In the above referred to prior art examples of chemical, electrochemical, and photochemical milling, the effect known as "undercutting", has been considered a serious defect and a limiting mechanism for the accuracy and resolution of chemical milling operations. Undercutting occurs when the chemical etchant removes metal beyond the boundary of a maskant, or resist layer. Often, such undercutting limits the fine resolution needed for many processes, such as the production of electronic devices, rotogravure plates, and other fine parts. However, undercutting may be exploited and utilized to produce useful and novel three-dimensional geometries by allowing the undercutting effect to expand deeper regions of a chemically applied pattern, so that the resulting treatment layer is an engineered pattern of undercut recesses. This provides sharp geometries when desired, and produces a higher void volume and larger fractal dimensions than are obtainable by other methods. Further, it permits retention of a predetermined area of original surface to afford an engineered and repeatable "datum surface", or surface intended to abut another body to which the undercut surface will be attached. The metal of the complex pattern is identical and contiguous with the base metal of the treated body, inasmuch as it is generated in the body, and not later applied, such as the fused metal spheres mentioned hereinabove.

While the method described herein is described in terms of producing textured metal surfaces, and while it is expected that the method will find substantial utility in metal bodies, and while the method produces deeply textured surfaces in metals, such as titanium, zirconium, stainless steel and alloys thereof, tantalum, refractory metals, metal carbides, and cobalt/chromium, it will be appreciated that the method is readily adapted for use with bodies of other materials including ferrous and non-ferrous metals, and alloys thereof, and ceramics, plastics and glass, and composites of metals, ceramics, plastics, and glass.

Figure 1:
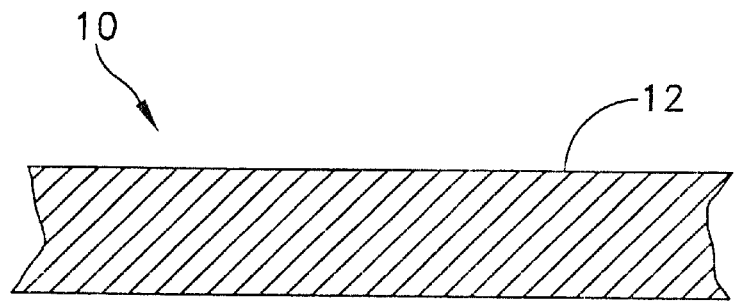
FIG. 1 is a diagrammatic sectional view of an article having a surface in which it is desired to provide a multiplicity of undercut micro recesses.

Referring to FIG. 1, it will be seen that there first is provided an article 10 of one of the above-mentioned materials, or a material similar thereto. The article 10 is provided with a datum surface 12 in which it is desired to provide a multiplicity of undercut recesses.

Figure 2:
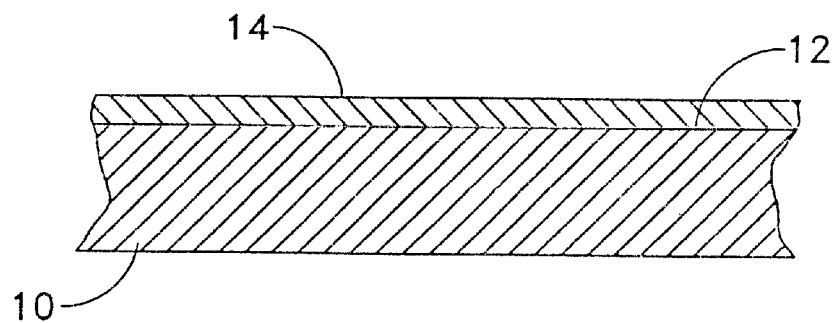
FIG. 2 depicts the article of FIG. 1 with a layer of maskant material deposited on the aforesaid surface.
Figure 3:
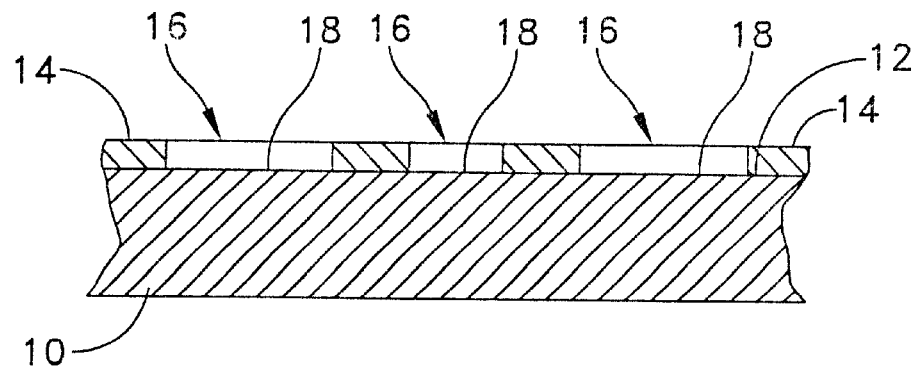
FIG. 3 depicts the article and maskant layer of FIG. 2 with the maskant layer in part removed.

As shown in FIG. 2, a layer 14 of maskant material is deposited on substantially the entirety of the surface 12. The maskant is a suitable acrylic, epoxy, or polyester resist, or the like. The layer 14 may be applied by dipping, spray coating, or electrostatic depositing, to produce a layer thickness of about 0.001–0.010 inch. The coated article of FIG. 2 preferably is baked at 200° F. (±10° F.) for about 15–17 minutes. Kodak Thin Film Resist has been found to be a quite suitable maskant. To the Kodak Resist is added 2%, by weight, carbon black pigment, or other pigment described hereinbelow.

Dispersing an appropriate pigment or dye into a maskant layer can render the maskant laser receptive. The maskant is selected based on the wavelength of the laser, or any projected light source, to be used to produce the desired pattern of maskant 14 on the surface 12. In the case of an infrared laser, the resulting local heating from the absorption of laser energy selectively removes tiny areas of the resist or maskant layer 14, thereby exposing the underlying metal surface 12 of the article to the action of an etchant. As noted above, a preferred maskant is Kodak Resist, to which is added 2% carbon black pigment, or other pigment more particularly suited to the laser wavelength to be employed. The pigment is dispersed into the maskant in a high shear mixer until fully dispersed, or until a temperature rise of 15–20° C. is reached. The resulting maskant is applied by dipping or by spraying, spinning, brushing or electrostatically depositing onto the surface to be treated.

Selected areas 16 of the layer 14 are then removed to expose portions 18 of the datum surface 12. The use of computer-directed direct laser ablation to generate programmed patterns in the maskant layer allows the application of such patterns to irregularly shaped finished goods, parts, or items which have surfaces of compound curves or radii. Such shapes are routinely encountered in implantable medical devices, such as dental post implants, hip joint assemblies, and maxillofacial prosthetics.

To generate a selected image, or array of recesses, or a fractal pattern, in a laser receptive maskant, the use of a computer-directed laser to directly ablate the maskant or etch resist layer in selected loci is preferred.

In a preferred embodiment of the method, ablations are made by direct writing with a neodymium-doped YAG laser with a wavelength of 1.06 microns, to which carbon black is receptive. A pattern is selected which optimizes the effects of undercutting. The pattern chosen is saved in Tagged Image File Format (TIFF) or as a plot (PLT) graphics file, and used to direct a laser marker.

An Electrox, Scriba Nd:YAG laser marker may be used, with patterns stored in digital file format. Upon laser exposure, the underlying surface portions 18 are exposed in those areas in which the maskant absorbs the laser beam.

The pattern produced by laser ablation is predictable and can be accurately duplicated and repeated from implant to implant. While the aforementioned YAG laser has been found effective, so also have $CO_2$, diode pump, and green lasers. Any laser capable of ablating, or thermally vaporizing, the maskant to generate a desired pattern of exposed surface may be used in carrying out the method described herein.

The pattern can be generated on a Computer Aided Design (CAD) system using any compatible file type, or generated as a phototool for imaging. The pattern can be scanned from a drawing, print, photograph, or the like, and converted into any file type compatible with the laser system employed.

An alternative method of manufacture is to use a photo sensitive maskant, which is applied to the device as stated above, or applied as a dry film which is laminated to the surface. The maskant is then exposed, using a light source of an appropriate wavelength (typically 280–550 nanometers). Portions of the maskant are cross-linked and/or bonded to the surface during the exposing process (in the case of negative working resist). The other areas of the maskant are dissolved or washed away in a developing process that utilizes a compatible developer solution, such as sodium or potassium carbonate, or stoddard solvents, thereby exposing the underlying material.

Figure 4:
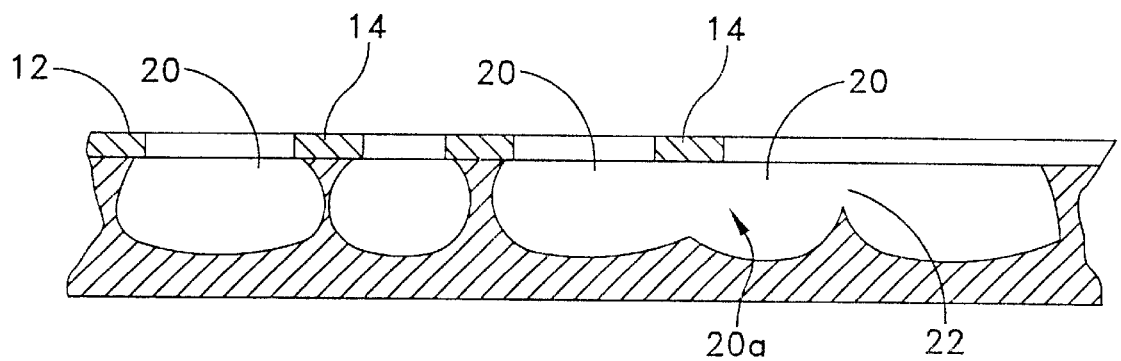
FIG. 4 is similar to FIG. 3 and showing portions of the article not covered by maskant etched away to provide undercut and interconnected recesses.
Figure 5:
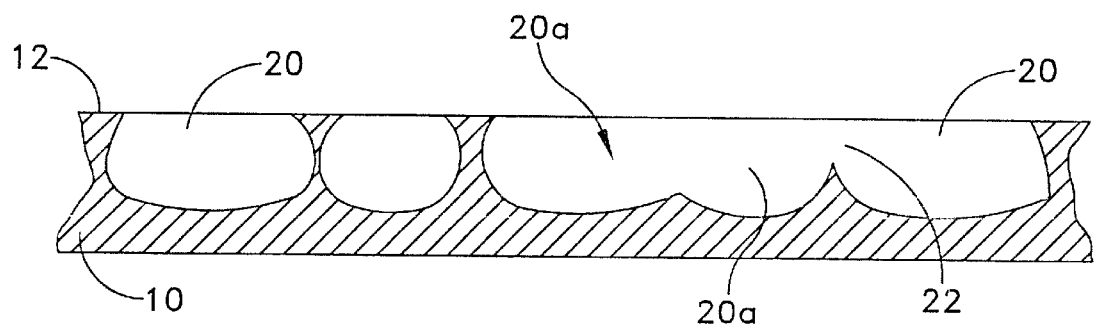
FIG. 5 is similar to FIG. 4, but showing the remaining maskant layer stripped away.

The exposed portions 18 of the surface 12 are etched, preferably using a spray etcher at 100° F. spray temperature and 10 lbs/in$^2$ spray pressure, in a Nitric and Hydrofluoric Acid solution for about 20 minutes. Sufficient "fresh" etchant is continuously impinged upon the etch surfaces 18 to encourage lateral, as well as vertical etching. It will be understood that alternative etching processes, such as immersing ultrasonics and electrolytic etching, can produce similar results. The etching produces recesses 20 which are undercut, as shown in FIG. 4, and which are, in part, interconnected, as at 22. The metal is etched in such a manner as to deliberately cause undercutting of the pattern, and to permit connection, joining, or "breakthrough" of some of the recesses so as to produce a sharply defined complex network structure, including an interconnecting pattern in which the size of most of the recesses is smaller at the surface 12 than at a plane some distance below the surface 12 of the article 10. The recesses 20 may, in at least some instances, interconnect at and near the surface 12, as at 22 in FIG. 4, to provide enlarged surface recesses 20a (FIG. 5).

The etching of the metal surface 12 is thus carried out in one step, as opposed to repetitive etching suggested in some of the prior art references cited hereinabove. In the one-step etching process, non-spherical ovoid shaped recesses are created featuring desired sizes and depths which are repeatable from implant to implant.

The remaining resist may be removed by immersing the body surface in a NU/Phase 23 Stripper bath at about 180° F. for about 10 minutes. Alternatively, the maskant layer may be removed (FIG. 5) by solvation or emulsification. If desired, the article 10 may be lightly post-etched.

There is thus provided a method for producing a complex, at least in part interconnecting pattern, or similar 3-dimensional surface treatment, to enhance the attachment of biological matter to a surface of an implantable device, or the interconnection of other bodies to be bonded, made by selective etching and undercutting of a surface so as to form a network of at least in part interconnected recesses. The pattern is formed by the direct laser ablation of an etch resist or maskant layer, allowing the textured surface to be applied to items with complex or curved surface geometries. The pattern is stored in a CAD or other computer-based system which controls the maskant ablations and is predictable and subject to repetitive duplication. The article is chemically etched to form the complex pattern. The metallurgical properties of the material of the article are not altered by heat, but remain substantially consistent during the process. Soft tissue or bone may in-grow the surface so produced, resulting in an interpenetrating network that offers superior mechanical adhesion and resistance to degradation. Further, the sharp edges at the intersections of the undercut recesses and the original datum surface facilitate an initial "scratch-fit" between the implant surface and a bone.

Figure 6:
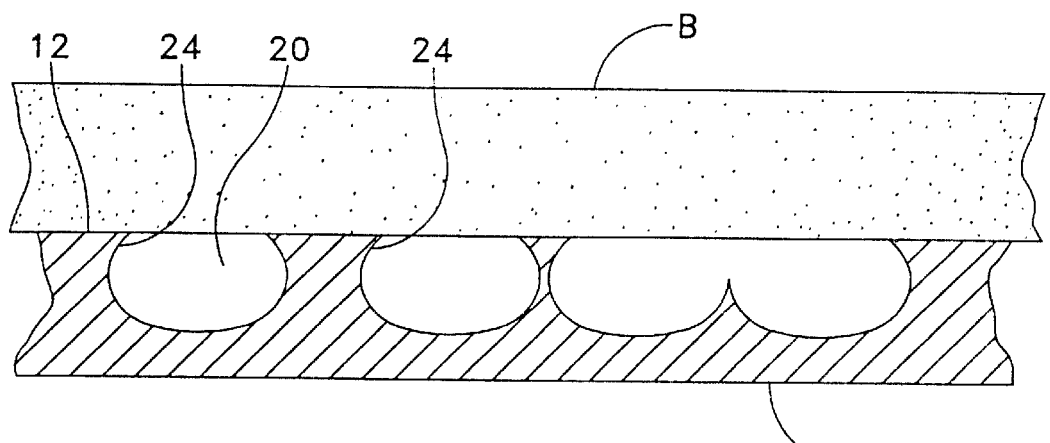
FIGS. 6–10 are progressive diagrammatic sectional views showing positioning of the article adjacent a bone and interconnection of the article and the bone.
Figure 7:
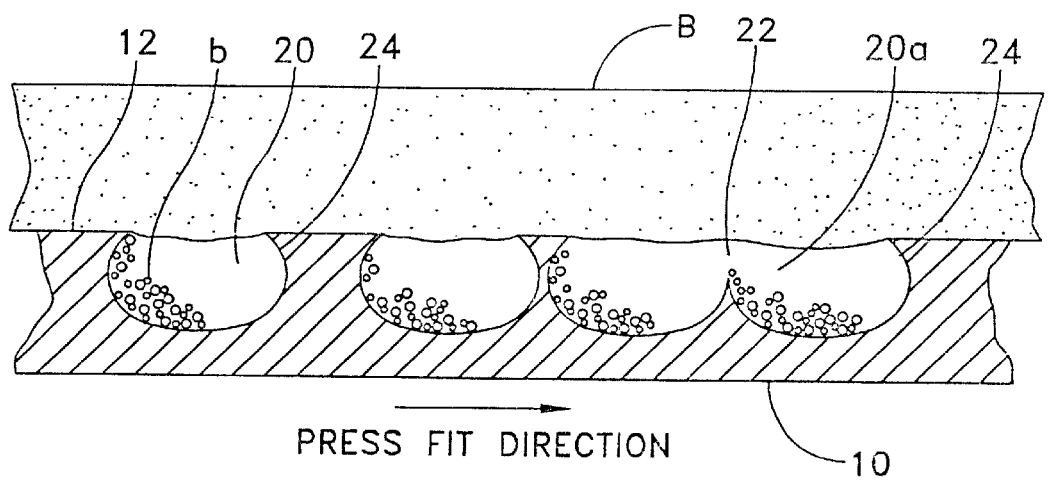
Figure 8:
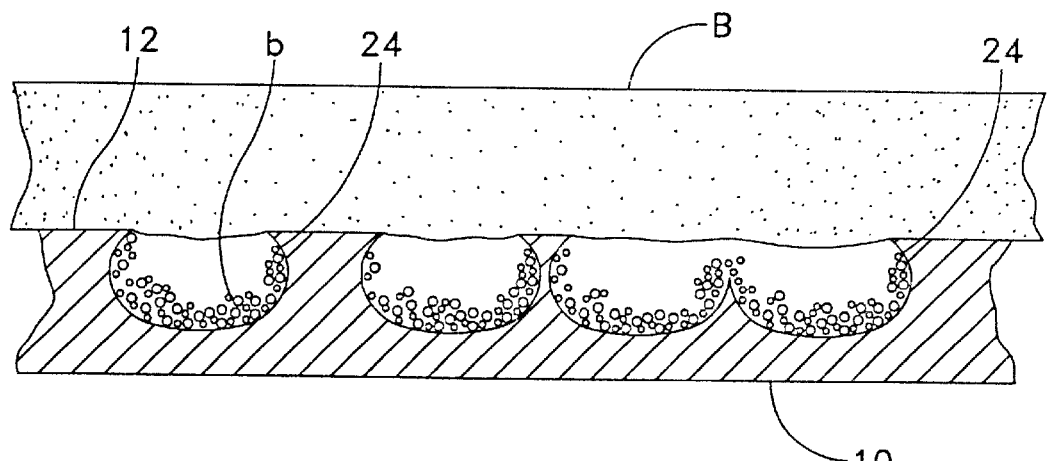
Figure 9:
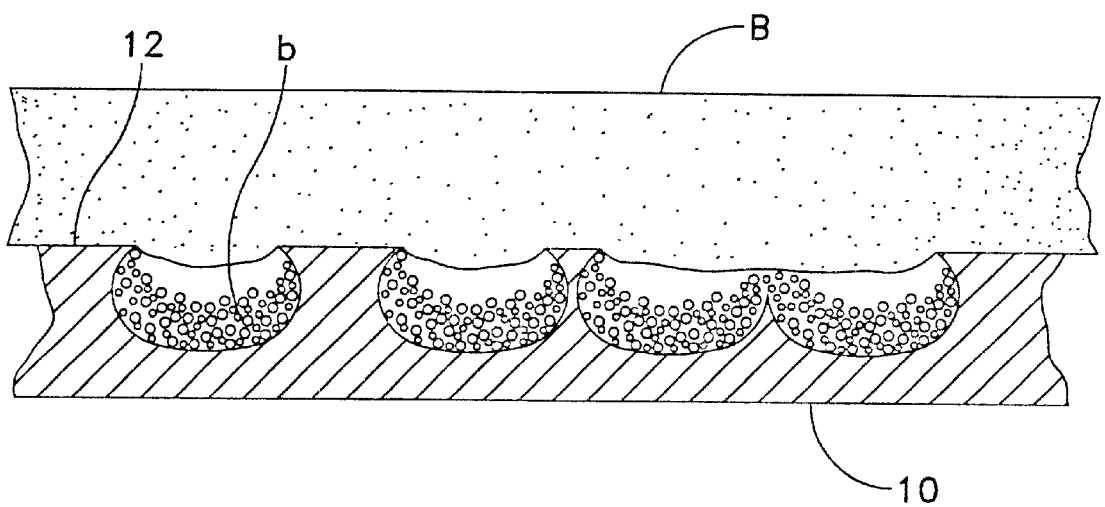
Figure 10:
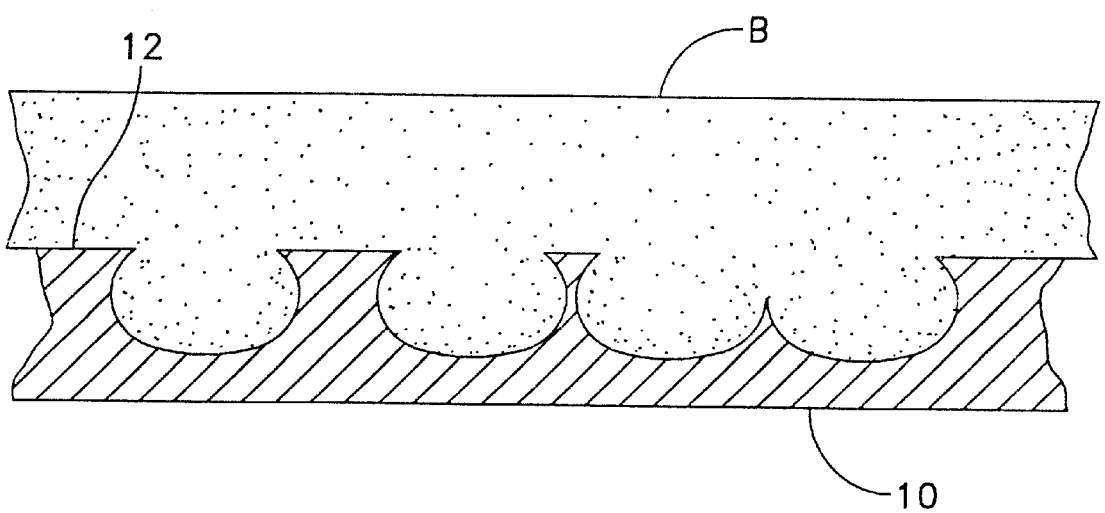

In operation, to produce a textured surface on a surgical implant, a selected pattern of undercut and at least in part interconnected recesses is effected in a surface of the surgical implant (FIG. 5). In implantation, the implant surface 12 is pressed against the bone B, (FIG. 6) such that sharp edges 24 of the recesses effect the "scratch fit" with the bone B, which involves shaving off, or milling, particulate segments b of the bone B, which segments b enter the ovoid recesses 20 wherein, in due course, the bone segments b stimulate in-growth of the bone B (FIG. 7) to securely lock the implant to the bone B (FIG. 8).

Thus, the scratch-fit securely adjoins the implant article 10 to the bone B, to prevent or minimize micro motion between the body 10 and bone B. The presence of such motion would discourage the ingrowth of bone into the implant and thereby discourage the long-term interconnection of the implant and bone.

Further, the scratch-fit application of the implant to the bone harvests bone particulate matter which falls into the surface recesses and is retained by the recesses to encourage and stimulate ingrowth of the bone into the recesses. Inasmuch as the recesses are of an ovoid configuration, they provide a greater sub-surface fractal area than spherically shaped recesses, and thereby a greater area for engagement of the bone material and the implant.

Figure 11:
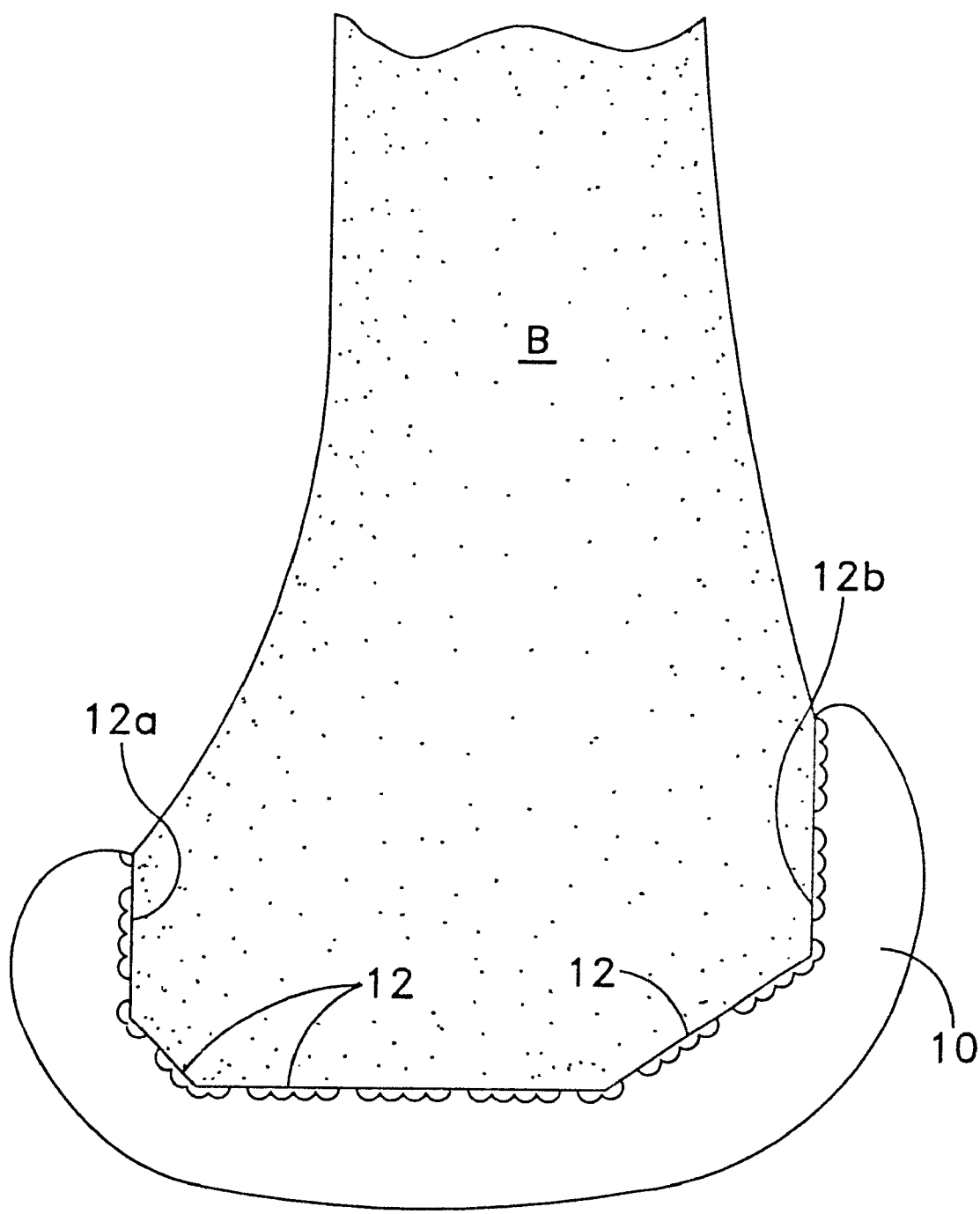
FIG. 11 is a diagrammatic sectional view of a surgical implant having a plurality of surfaces treated as illustrated in FIGS. 2–10.

Referring to FIG. 11, it will be seen that for bones B accepting an implant 10 having a plurality of datum surfaces 12, including opposed surfaces 12a and 12b, the accurate location of the datum surfaces is most critical, inasmuch as any build-up of implant material above the datum surfaces causes the implant not to be accepted by the bone B. Texturing the surfaces 12 below the surfaces does nothing to add to the surfaces. Whereas, texturing the surfaces 12 above the surfaces increases the space required between the opposed bone surfaces to accept the implant and leads to rejection of the implant. Known methods of texturing by adding to a surface lack the required precise control to determine the deviation of the peaks of the added material. The method presented herein facilitates accurate and precise location of datum surfaces of surgical implants.

Other applications in industry and manufacturing will be apparent for such sharpened surfaces, including dental drills, surgical rasps, medical files and burrs, and cutting tools generally.

It will be understood that many additional changes in the details, materials, steps and arrangement of parts, which have been herein described and illustrated in order to explain the nature of the invention, may be made by those skilled in the art within the principles and scope of the invention. For example, while the recesses are shown with a central axis normal to the datum surface, it will be apparent that the recess axes can be "tilted" to provide asymmetrical undercutting. By impinging the etchant at an angle, a tilted saw-tooth structure (not shown) can be realized. Such structure allows relatively easy insertion into a bone channel, but strongly resists tensile force urging dislodgement of the implant.

What is claimed is:

1. A surgical implant comprising:
    a base having an integral datum surface for engaging tissue; and
    a multiplicity of interconnected recesses in the datum surface, the recesses comprising a sharp undercut ovoid pattern.

2. The implant of claim 1, wherein the datum surface is an original datum surface.

3. The implant of claim 1, wherein the multiplicity of interconnected recesses form a complex network structure.

4. The implant of claim 1, wherein the sharp undercut ovoid pattern is adapted to shave the tissue.

5. The implant of claim 1, further comprising a base material, the sharp undercut ovoid pattern being integral with the base material.

6. The implant of claim 1, wherein the undercut ovoid pattern is repeatable from implant to implant.

* * * * *